mixing chamber to blend with the first mixture of the carrier gas and

(12) United States Patent
Matthews et al.

(10) Patent No.: US 9,506,898 B1
(45) Date of Patent: Nov. 29, 2016

(54) DEVICE FOR CONTROLLED VAPOR GENERATION

(71) Applicant: U.S. Army Edgewood Chemical and Biological Command, APG, MD (US)

(72) Inventors: Robin L. Matthews, Port Deposit, MD (US); Kwok Y. Ong, Joppa, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 344 days.

(21) Appl. No.: 14/163,636

(22) Filed: Jan. 24, 2014

Related U.S. Application Data

(60) Provisional application No. 61/793,974, filed on Mar. 15, 2013.

(51) Int. Cl.
*G01N 33/00* (2006.01)
(52) U.S. Cl.
CPC ....... *G01N 33/0006* (2013.01); *G01N 33/0004* (2013.01); *Y10T 436/25625* (2015.01); *Y10T 436/25875* (2015.01)
(58) Field of Classification Search
CPC .................................................. G01N 33/0006
USPC ......................................................... 436/181
See application file for complete search history.

(56) References Cited

U.S. PATENT DOCUMENTS

| 3,976,450 A * | 8/1976 | Marcote | G01N 1/34 128/205.12 |
| 4,774,032 A * | 9/1988 | Coates | A61M 16/18 128/204.13 |
| 5,157,957 A * | 10/1992 | Mettes | B01F 3/026 137/7 |
| 5,728,927 A * | 3/1998 | Ong | G01N 33/0006 73/1.02 |
| 7,418,881 B2 * | 9/2008 | Watson | G01N 1/38 73/865.5 |

* cited by examiner

*Primary Examiner* — Christopher A Hixson
*Assistant Examiner* — Emily Berkeley
(74) *Attorney, Agent, or Firm* — Ulysses John Biffoni

(57) ABSTRACT

A device and method for generating vapor concentrations of a chemical. The device comprises a reservoir including a mixing chamber and a delta tube inlet section attached to the mixing chamber for supplying a first mixture of a carrier gas and a vapor of the chemical to the mixing chamber. A dilution gas inlet section is also attached to the mixing chamber and supplies a stream of dilution gas to the mixing chamber to blend with the first mixture of the carrier gas and the vapor of the chemical resulting in a second mixture of the carrier gas, the vapor of the chemical, and the dilution gas. An exit port section attached to the mixing chamber directs the second mixture of the carrier gas, the vapor of the chemical, and the dilution gas to an analyzer or system after it emerges from the reservoir.

11 Claims, 4 Drawing Sheets

DEVICE FOR CONTROLLED VAPOR GENERATION

CROSS-REFERENCE TO RELATED APPLICATIONS

This application claims the benefit of priority from U.S. Provisional Application Ser. No. 61/793,974 filed on Mar. 15, 2013.

GOVERNMENT INTEREST

The invention described herein may be manufactured, used and licensed by or for the United States Government.

TECHNICAL FIELD OF THE INVENTION

The present invention relates to a device for generating vapor concentrations of a chemical and more particularly to a device and method for generating vapor concentrations of a chemical utilizing a reservoir.

BACKGROUND OF THE INVENTION

Methods to produce precisely controlled concentrations of chemical warfare (CW) agents and toxic industrial chemicals, or any chemical vapors using control streams of air, nitrogen, and other carriers are crucial for evaluating the performance of systems and equipment used to protect military combatants or civilians who might be exposed to environments containing these materials. Examples of protective equipment that rely on these methods include chemical vapor filtration and detection systems. Chemical vapor generator systems have been used in the art for calibrating and testing the agent sensitivity of such chemical devices and monitors. A number of methods have been developed for performing such tests and calibrations.

The ability to generate stable vapor concentrations of target analytes has been developed with various techniques to test detection devices within the laboratory environment. Several well-known methods of vapor generation are carried out by using direct contact of the chemical with a carrier gas stream. These include sparging, syringe injection of the liquid material directly into a carrier gas flow stream, and vapor saturation. "Indirect" methods, where a barrier is introduced between the chemical and its vapor, such as permeation, diffusion, and effusion have also been used.

SUMMARY OF THE INVENTION

According to an embodiment of the present invention, there is disclosed a device for efficient generation of vapor concentrations of a chemical. The device comprises a reservoir which combines a mixing chamber and a delta tube inlet section attached to the mixing chamber for supplying a first mixture of a carrier gas and a vapor of the chemical to the mixing chamber. In addition, a dilution gas inlet section attached to the mixing chamber supplies a stream of conditioned dilution gas to the mixing chamber to blend with the first mixture of the carrier gas and the vapor of the chemical resulting in a second mixture comprising the carrier gas, the vapor of the chemical, and the dilution gas at the desired condition. An exit port section attached to the mixing chamber is adapted to direct the second mixture of the carrier gas, the vapor of the chemical, and the dilution gas to form a targeted concentration for testing of an analyzer or protection system after it emerges from the device.

According to another embodiment of the present invention, there is disclosed a method for generating vapor concentrations of a chemical. The method includes first supplying a first mixture of a carrier gas and a vapor of the chemical to a mixing chamber. Second, supplying a stream of dilution gas to the mixing chamber to blend with the first mixture of the carrier gas and the vapor of the chemical resulting in a second mixture of the carrier gas, the vapor of the chemical, and the dilution gas. Third, directing the second mixture of the carrier gas, the vapor of the chemical, and the dilution gas after it emerges from the reservoir.

According to still another embodiment of the present invention, there is disclosed a system for generating vapor concentrations of a chemical. The system includes a mixing chamber and a delta tube inlet section attached to the mixing chamber for supplying a first mixture of a carrier gas and a vapor of the chemical to the mixing chamber with a source of carrier gas connected to the mixing chamber by the delta tube inlet section. A dilution gas inlet section is also attached to the mixing chamber for supplying a stream of dilution gas to the mixing chamber to blend with the first mixture of the carrier gas and the vapor of the chemical resulting in a second mixture of the carrier gas, the vapor of the chemical, and the dilution gas, with a source of dilution gas connected to the mixing chamber by the dilution gas inlet section. An exit port section attached to the mixing chamber directs the second mixture of the carrier gas, the vapor of the chemical, and the dilution gas to an analyzer to test the concentration of the chemical after it emerges from the reservoir.

BRIEF DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

Figure 1:
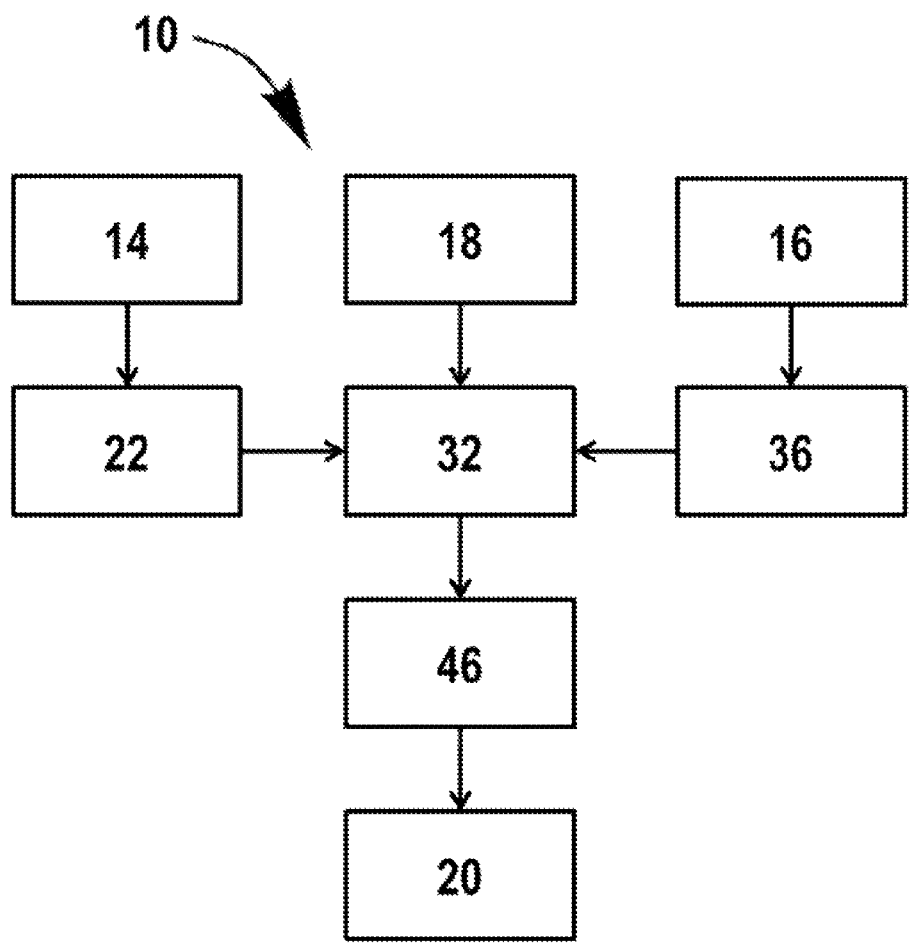
FIG. 1 is a schematic view of the system for controlled vapor generation, in accordance with the present invention.
Figure 2:
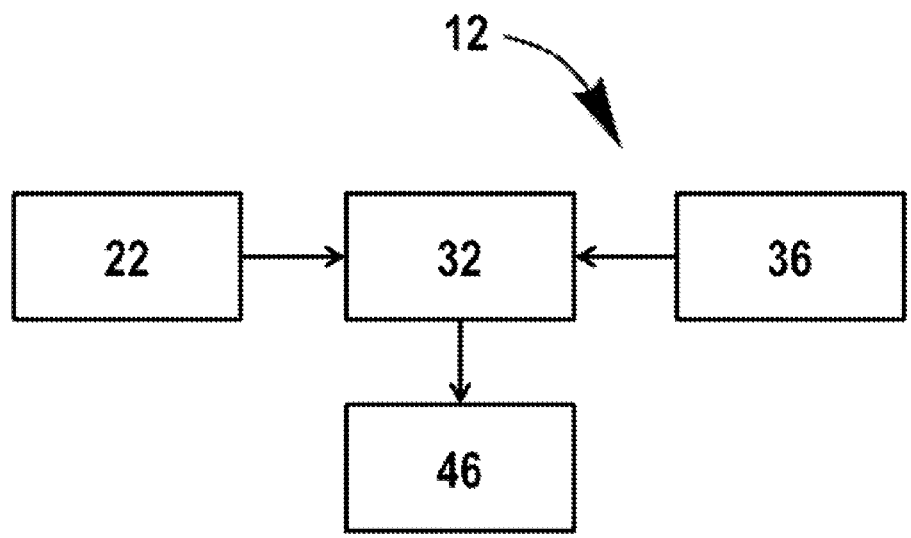
FIG. 2 is a schematic view of the device of the system for controlled vapor generation, in accordance with the present invention.
Figure 3:
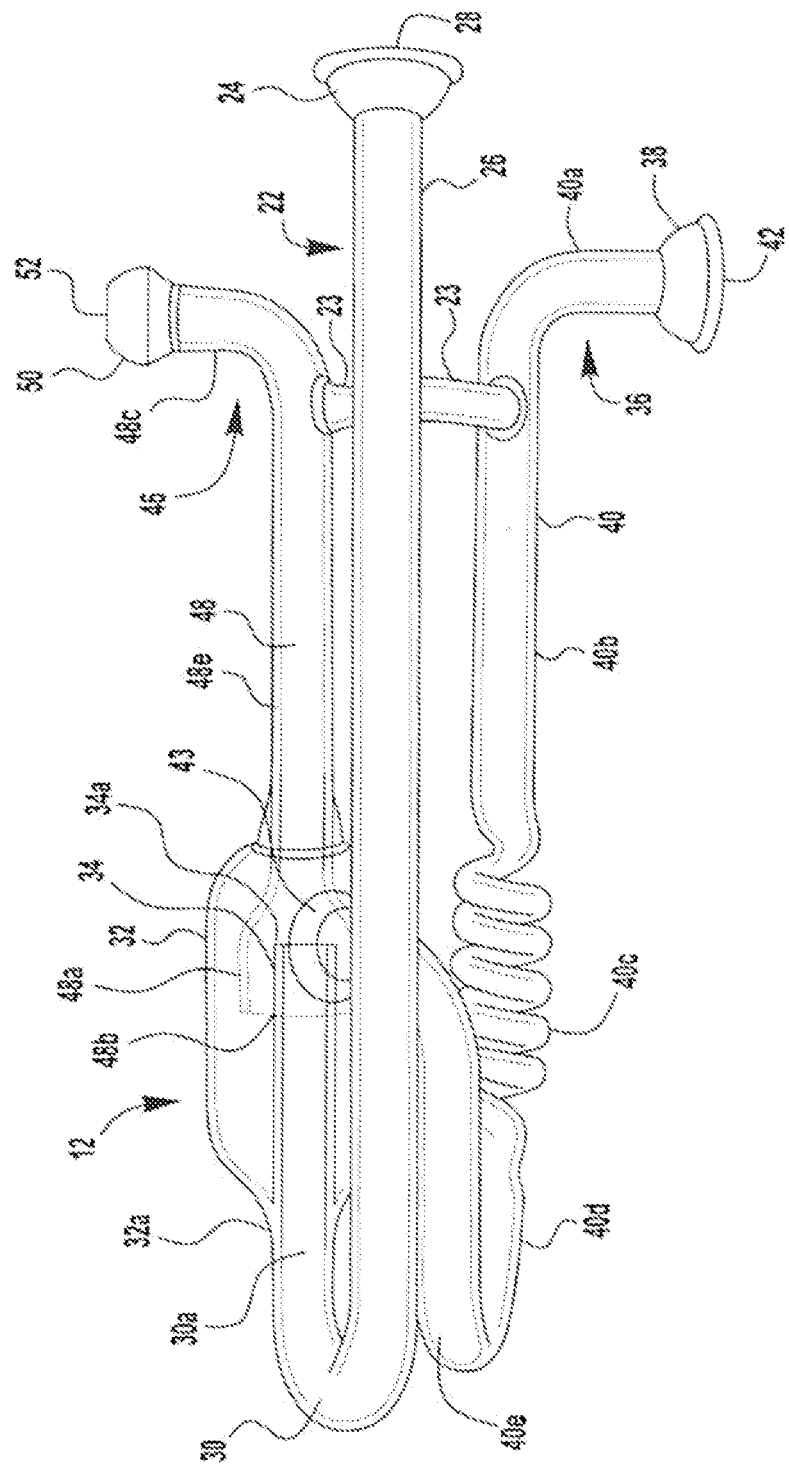
FIG. 3 is a front three dimensional view of the device for use with the system for controlled vapor generation, in accordance with the present invention.

In the description that follows, numerous details are set forth in order to provide a thorough understanding of the present invention. It will be appreciated by those skilled in the art that variations of these specific details are possible while still achieving the results of the present invention.

Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

The most common and proven technique of generating stable vapor concentrations of target analytes is to pass a volume of air or carrier gas over a droplet of neat material. The headspace vapor is carried into a dilution manifold to achieve the concentration level. Detectors can then be tested with this concentration stream accordingly. The amount of headspace vapor of the neat material depends on the relative volatility of the material at a specific temperature. Many materials have very low volatility. Thus, the headspace vapor concentrations at ambient temperatures are low, preventing the ability to dilute into the larger volume generation required by many detection devices. Consequently, it is necessary to increase the temperature of the reservoir, usually with a heated bath, to produce the required vapor concentrations of a low volatile compound to meet the concentrations generation requirement. The traditional reservoir for holding the neat material is a delta-shaped glass tube which is immersed in the temperature bath, and the exhaust is plumbed into the dilution manifold, outside the bath. With the test apparatus in this configuration, condensation of the material occurs once the hot vapor cools upon leaving the heated zone prior to entering the dilution manifold. Once condensation forms, the heating benefit to generate higher vapor concentration available for proper dilution has been lost. A substantial portion of the additional vapor from the heated reservoir will be absorbed by the condensate limiting the vapor concentration dictated by the condensate volatility at that ambient temperature.

FIG. 1 illustrates a schematic view of the system for closed vapor generation (hereafter "system") 10, specifically designed to alleviate issues associated with condensation. In general terms, system 10 is designed to generate stable vapor concentrations of a chemical, especially those chemicals with low volatilities. It is within the terms of the embodiment that the system 10 is used to generate stable vapor concentrations of a chemical agent. The system 10 includes a mixing chamber 32 (as discussed in more detail below), a source of carrier gas 14 connected to the mixing chamber 32 by a delta tube inlet section 22, a source of dilution gas 16 connected to the mixing chamber by a dilution gas inlet section 36, an analyzer 20 connected to the mixing chamber 32 by an exit port section 46 and a heat source 18. The system 10 is designed to prevent the condensation of low volatility materials in the system by heating and blending the mixture of the dilution gas, the carrier gas and the chemical prior to exiting the exit port section 46, thereby avoided the condensation issue and allowing higher generated vapor concentrations of these materials to meet the challenges. System 10 will extend the ability to achieve the desired expanded range of realistic vapor concentration generation. Utilizing system 10 will allow for most of the same vapor generation procedures can be followed without the loss of control over the vapor concentration being produced.

In a preferred embodiment, as shown in FIGS. 2 and 3, the device 12 includes a mixing chamber 32 having the delta tube inlet section 22, the dilution gas inlet section 36, and the exit port section 46 connected thereto. At least a portion of the device 12 is maintained within a heat source 18. For example, device 12 may be immersed in a temperature controlled heat bath, or encased in a heat exchange jacket to maintain a constant desired temperature of the neat material, such as a chemical. The surrounding ambient temperature dictates the vapor concentration available for dilution to produce the final concentration at a certain volume capacity. Preferably, the desired concentration of the chemical vapor is less than the chemical's volatility at the temperature of the ambient air in order to avoid liquid condensation of the effluent.

The source of carrier gas 14 connected by a delta tube inlet section 22 to the device 12 supplies a precisely controlled carrier gas that carries the headspace vapor of the chemical agent through the device, diluted with the dilution flow from 40*e* in the manifold 32 for eventual testing and analysis by the analyzer 20. The source of carrier gas 14 may provide any appropriate gas, such as nitrogen, and may include a fine needle valve flow meter or flow controller. The carrier gas mixes with the chemical vapor as it flows over the chemical and forms a mixture of carrier gas and chemical vapor that flows into the mixing chamber 32.

The source of dilution gas 16 is connected by dilution gas inlet section 36 to the mixing chamber 32 and supplies a stream of dilution gas, typically air, to the mixing chamber to blend with the mixture of carrier gas and chemical vapor prior to exiting the mixing chamber 32 through the exit port section 46. By heating the device 12 with a heat source 18, such as by submerging the device 12 in a heated bath, condensation is prevented from forming when dealing with low volatility agents. The resulting vapor concentration after the dilution will be less than the volatility of the substance at the ambient temperature of the exit port 48*c*, thereby condensation is avoided. By preventing the formation of a condensation of the vapor at the test temperature, the issues hindering the generation of a higher vapor concentration of the low volatile chemical is substantially reduced. System 10 is specifically designed to eliminate condensation issues and permit a successful higher vapor concentration generation which is a necessity for the low volatile substances.

Analyzer 20 may be used to analyze the concentration of the chemicals in the mixture of the dilution gas, the carrier gas, and the vapor of the chemical after it emerges from the mixing chamber through the exit port section 46.

FIG. 3 illustrates a detailed view of the device 12. Device 12 has three connecting port sections connected to mixing chamber 32, the delta tube inlet section 22, the dilution gas inlet section 36 and the exit port section 46 (dilution gas inlet section 36 and the exit port section 46 are described below). The delta tube inlet section 22, the dilution gas inlet section 36 and the exit port section 46 are secured to each other with solid glass struts 23. The delta tube inlet section 22 has an inlet opening 28 typically formed as a first female ground glass joint 24, followed by a straight glass portion 26. The straight glass portion 26 may be any length, but is preferably approximately eight inches long. Straight glass portion 26 must be straight to allow the deposition of chemicals deep in the tube.

Glass joint 24 is connected to the source of carrier gas 14 to allow a stream of carrier gas to enter into the device 12 through an inlet opening 28. Straight glass portion 26 contains a small volume of chemical, typically in liquid form, in an amount such that the liquid only occupies a bottom segment of the straight glass portion. This volume of chemical fills only a portion of the straight glass portion 26 so as not to completely seal the tube with liquid, allowing for a continuous flow of carrier gas from the first glass joint 24 to the remainder of the device 12. The end of the straight glass portion 26 takes approximately a 180-degree turn, creating a curved inline reservoir 30 for the chemical whereby the curved inline reservoir of the delta tube inlet section forms an approximate 180-degree turn between the straight glass portion and the outlet segment so that the outlet segment 30a extends generally parallel to the delta tube inlet section 22.

Figure 4:
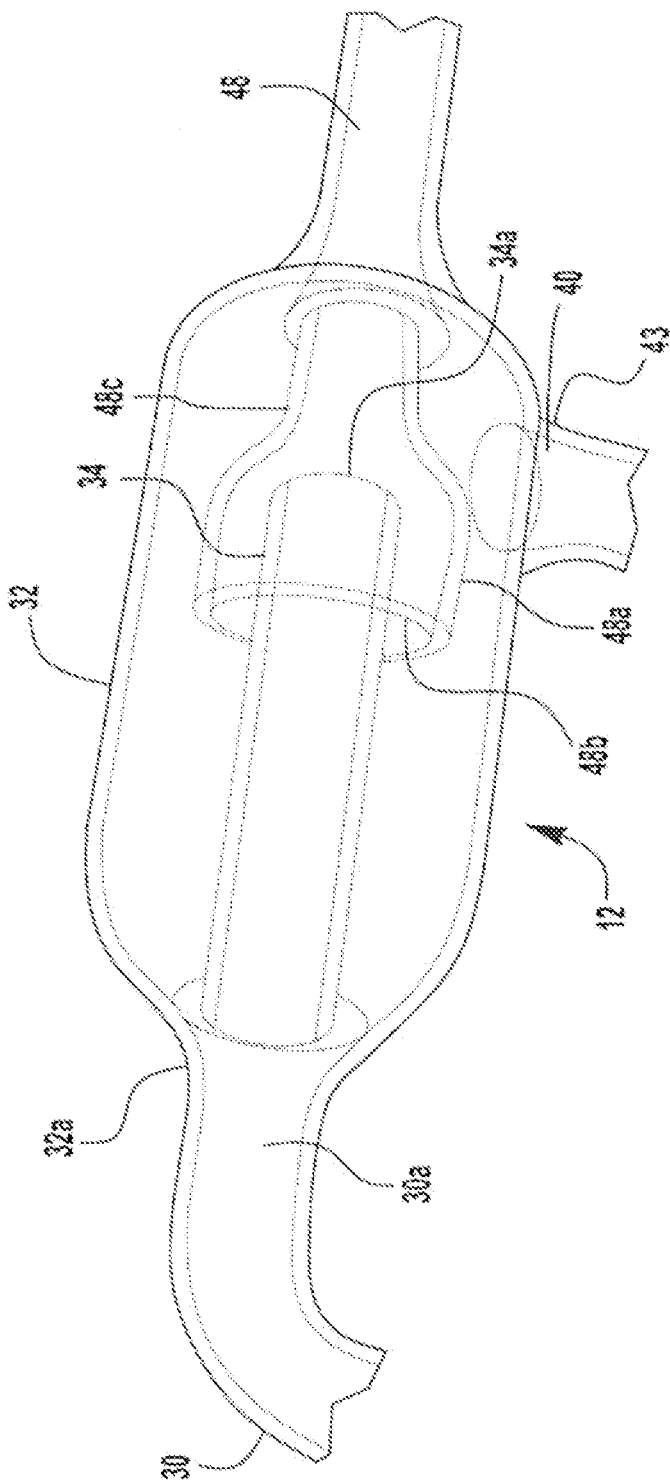
FIG. 4 is a front three dimensional view of the mixing chamber of the device, in accordance with the present invention.

FIG. 4 illustrates the mixing chamber 32, which extends from an outlet segment 30a of the curved inline reservoir 30 and has a larger diameter than the curved inline reservoir. Mixing chamber 32 has an inlet opening 32a into which an exit section 34 of the delta tube inlet section 22 extends. This exit section 34 extends approximately 1 inch after the curved inline reservoir 30. There is an outlet opening 34a in the exit section 34 through which a first mixture of a carrier gas and a vapor of the chemical flows into a cup shaped first section 48a of the exhaust tube 48, as discussed herein after.

Further, mixing chamber 32 is connected to the dilution gas inlet section 36. The dilution gas inlet section 36 is formed of a second female ground glass joint 38 followed by a dilution gas tube portion 40. The dilution gas tube portion 40 extends between the glass joint 38 and the mixing chamber 32. Second glass joint 38 is connected to the source of dilution gas 16 to allow a stream of air to enter into the device 12 through an inlet opening 42 within the second glass joint and then through the dilution gas tube portion 40 into the mixing chamber 32.

The dilution gas tube portion 40 is generally oriented parallel to the delta tube inlet section 22, but has a first section 40a, connected to the glass joint 38, extending generally perpendicular to the straight glass portion 26. A first straight line section 40b extends generally parallel to the straight glass portion 26. The dilution gas tube portion 40 features a spiral portion 40c generally adjacent to the mixing chamber 32. This spiral portion 40c is designed to allow incoming dilution air more time to equilibrate to the temperature of the heat source 18 before entering the mixing chamber 32. For this reason, the curved inline reservoir 30 holding the chemical, the mixing chamber 32 and the spiral portion 40c are designed to be completely enveloped within the heat source 18.

Downstream from the spiral portion 40c is a second straight line section 40d. Second straight line section 40d takes an approximate 180-degree turn and forms a third straight line section 40e. The dilution gas tube portion 40 has an outlet opening 43 at the opposite end of dilution gas tube portion 40 from the inlet opening 42, terminating at the mixing chamber 32, to allow the dilution gas to flow into the mixing chamber. It is through outlet opening 43 that the air stream created by the source of dilution gas 16 enters into the mixing chamber 32.

Further, mixing chamber 32 is connected to the exit port section 46. The exit port section 46 is formed of an exhaust tube 48, which is connected to an exit port 50. The vapor concentration, upon leaving the mixing chamber 32, exits through the exhaust tube 48 and continues through an outlet opening 52 in the exit port section 46, to be analyzed. The exhaust tube 48, which extends between the mixing chamber 32 and the exit port 50, is parallel to both the straight glass portion 26 of the delta tube inlet 22 section, and the first straight line section 40b of the dilution gas inlet section 36. The exhaust tube 48 may be any desired length.

There is a first section 48a of the exhaust tube 48 extends into the mixing chamber 32, and through which the exit section 34 of the delta tube inlet section 22 extends. First section 48a has a cup shape open at one end 48b with a first diameter and a narrow neck 48c at the other end having a second diameter that is less than the first diameter. The narrow neck 48c extends through the wall of the mixing chamber 32 and into an intermediate section 48e of the exhaust tube 48. The cup shaped first section 48a with the narrow neck 48c are disposed towards an end of the mixing chamber so that the outlet opening 43 of tube portion 40 is adjacent the cup shaped first section 48a so that the dilution gas flowing into the mixing chamber first encounters the cup shaped first section 48a. Then the dilution gas is forced to flow around the cup shaped first section 48a and towards the inlet opening 32a of mixing chamber 32 before flowing into the opening 48b to mix with the first mixture of the carrier gas and the vapor of the chemical. The result is a second mixture including the carrier gas, the vapor of the chemical and the dilution gas exiting the mixing chamber 32 through the exhaust tube 48. The intermediate section 48e of exhaust tube 48 terminates with a 90-degree bend portion 48c before reaching the exit port 50. The analyzer 20, as shown in FIG. 1, is attached to the outlet opening 52 within the exit port 50 to make calculations based on the second mixture.

In use, the device 12 is at least partially ensconced within a heat source 18 to provide elevated temperature to increase the substance's volatility. A neat material, such as a chemical, is placed within the straight glass portion 26 of the delta tube inlet section 22. The source of carrier gas 14 supplies a carrier gas, such as nitrogen, through the inlet opening 28 and over the chemical within the straight glass portion 26. This creates a first mixture of carrier gas and the vaporized chemical.

The first mixture travels through the curved inline reservoir 30 and is carried into the mixing chamber 32 through the outlet opening 34a within the exit section 34. Meanwhile, source of dilution gas 16 supplies a stream of gas, such as conditioned air, through the dilution gas inlet section 36. The dilution air travels through the dilution gas tube portion 40, where it passes through the spiral portion 40c, until it reaches the mixing chamber 32 through outlet opening 43 of the dilution gas tube portion 40.

In the mixing chamber 32, the first mixture of the carrier gas and the vapor of the chemical mixes with the dilution gas to form a second mixture including the carrier gas, the vapor of the chemical and the dilution gas which is at approximately the same temperature as the first mixture. The vapor concentration of the chemical after being diluted with the dilution gas, however, will have a lower vapor saturation point of the chemical at the surrounding test temperature, thus avoiding condensation.

The second mixture including the carrier gas, the vapor of the chemical and the dilution gas exits the mixing chamber 32 through the exhaust tube 48, and departs the reservoir 12 through opening 52 of the exit port 50. Then, the analyzer 20, which is connected to the exit port 50, may detect the vapor concentration and conduct any desired analysis of the vapor concentration.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A device for generating vapor concentrations of a chemical, comprising:
    a mixing chamber;
    a delta tube inlet section directly, attached to the mixing chamber and having an outlet opening disposed inside the mixing chamber for supplying a first mixture of a carrier gas and a vapor of the chemical to the mixing chamber;
    a dilution gas inlet section directly attached to the mixing chamber and having an outlet opening located at the mixing chamber for supplying a stream of dilution gas to the mixing chamber to blend with the first mixture of the carrier gas and the vapor of the chemical resulting in a second mixture of the carrier gas, the vapor of the chemical, and the dilution gas; and
    an exit port section directly attached to the mixing chamber adapted to direct the second mixture of the carrier gas, the vapor of the chemical, and the dilution gas to an analyzer or system after it emerges from the device, and
    wherein the vapor concentration of the chemical after being diluted in said second mixture has a lower vapor saturation point so that the chemical will not condense after it emerges from the device and is directed to the analyzer or system.

2. The device of claim 1, wherein the exit port section has an exhaust tube with an inlet opening within a first section of the exhaust tube disposed within the mixing chamber and an outlet opening in a second section of the exhaust tube.

3. The device of claim 2, wherein the first section of the exhaust tube within the mixing chamber has a cup shape with a wide open end in the mixing chamber and with a narrow neck that extends through the wall of the mixing chamber and into an intermediate section of the exhaust tube.

4. The device of claim 3, wherein the delta tube inlet section has a straight glass portion with an inlet opening at one end followed by a curved inline reservoir having an outlet segment extending into the cup shaped first section of the exhaust tube within the mixing chamber.

5. The device of claim 4, wherein the curved inline reservoir of the delta tube inlet section forms a 180-degree turn between the straight glass portion and the outlet segment.

6. The device of claim 3, wherein the dilution gas inlet section has an inlet opening and an outlet opening extending through the wall of the mixing chamber adjacent the cup shaped first section of the exhaust tube within the mixing chamber.

7. The device of claim 6, wherein the dilution gas tube portion has a first section with the inlet opening, a first straight line section connected to the first section, a spiral portion that follows the first straight line section, and a second straight line section follows the spiral portion.

8. The device of claim 7, wherein the second straight line section of the dilution gas tube portion takes a 180-degree turn and forms a third straight line section with an outlet opening terminating through the wall of the mixing chamber to allow the dilution gas to flow into the mixing chamber in the direction of the cup shaped first section of the exhaust tube within the mixing chamber.

9. A system for generating vapor concentrations of a chemical, comprising:
    a mixing chamber;
    a delta tube inlet section directly attached to the mixing chamber and having an outlet opening disposed inside the mixing chamber for supplying a first mixture of a carrier gas and a vapor of the chemical to the mixing chamber;
    a source of carrier gas connected to the mixing chamber by the delta tube inlet section;
    a dilution gas inlet section directly attached to the mixing chamber and having an outlet opening located at the mixing chamber for supplying a stream of dilution gas to the mixing chamber to blend with the first mixture of the carrier gas and the vapor of the chemical resulting in a second mixture of the carrier gas, the vapor of the chemical, and the dilution gas;
    a source of dilution gas connected to the mixing chamber by the dilution gas inlet section; and
    an exit port section directly attached to the mixing chamber adapted to direct the second mixture of the carrier gas, the vapor of the chemical, and the dilution gas to an analyzer or system after it emerges from the system; and
    wherein the vapor concentration of the chemical after being diluted in said second mixture has a lower vapor saturation point to prevent condensation of the chemical after it emerges from the device and is directed to the analyzer or system.

10. The system of claim 9, further including a heat source to heat the first mixture of the carrier gas and the vapor of the chemical and the second mixture of the carrier gas, the vapor of the chemical, and the dilution gas to prevent condensation from forming.

11. The system of claim 10, wherein the heat source is a temperature controlled heat bath into which the delta tube inlet section, the dilution gas inlet section, and the mixing chamber are immersed.

* * * * *